(12) United States Patent
Vertesy et al.

(10) Patent No.: US 7,259,276 B2
(45) Date of Patent: Aug. 21, 2007

(54) POLYENECARBOXYLIC ACID DERIVATIVES, PROCESSES FOR PREPARING THEM, AND THEIR USE

(75) Inventors: László Vertesy, Eppstein-Vockenhausen (DE); Michael Kurz, Hofheim (DE); Joachim Wink, Rödermark (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 419 days.

(21) Appl. No.: 10/608,466

(22) Filed: Jun. 27, 2003

(65) Prior Publication Data

US 2004/0042981 A1 Mar. 4, 2004

Related U.S. Application Data

(60) Provisional application No. 60/423,473, filed on Nov. 4, 2002.

(30) Foreign Application Priority Data

Jul. 2, 2002 (DE) ................................. 102 29 713

(51) Int. Cl.
*C07C 59/00* (2006.01)
*C07C 323/02* (2006.01)
*C07C 229/00* (2006.01)
*C07C 69/76* (2006.01)

(52) U.S. Cl. ..................... 562/426; 562/450; 562/465; 560/81; 560/95

(58) Field of Classification Search .................. 424/59; 562/426, 450, 466; 560/81, 95
See application file for complete search history.

(56) References Cited

OTHER PUBLICATIONS

Darby et al., Synthesis of Benzannelated Bisdehydro[14]-,[16]-,[18]-,and -[20]annulenes, 1977, vol. 42, No. 11, p. 1960-1967.*

Darby N et al., Synthesis of Benzannelated Bisdehydro[14]-, -[16]-, -[18]-, and -[20]annulenes1, J. Org. Chem., vol. 42, No. 11, 1977, pp. 1960-1967.

Goldman R et al., Inhibition of Transglycosylation Involved in Bacterial Peptidoglycan Synthesis, Current Medicinal Chem., vol. 7, 2000, pp. 801-820.

Kurz M et al., Three-dimensional structure of moenomycin A. A potent inhibitor of penicillin-binding protein 1b, Eur. J. Biochem, vol. 252, 1998, pp. 500-507.

Ritzau M et al., Serpentene, a Novel Polyene Carboxylic Acid from Streptomyces, Liebigs Ann. Chem., 1993, pp. 433-435.

Stolph H, Dispersal of microorganisms and development of microbial populations, Microbial ecology: organismus, habitats, activities, Cambridge University Press, Cambridge, GB, Chapter 6, 1988, pp. 172-181.

Vollmer W et al., A Simple Screen for Murein Transglycosylase Inhibitors, Antimicrobial Agents and Chemotherapy, vol. 44, No. 5, 2000, pp. 1181-1185.

* cited by examiner

*Primary Examiner*—Taylor Victor Oh
(74) *Attorney, Agent, or Firm*—Irving Newman

(57) ABSTRACT

The present invention relates to novel compounds, termed serpentemycins, of the formula (I)

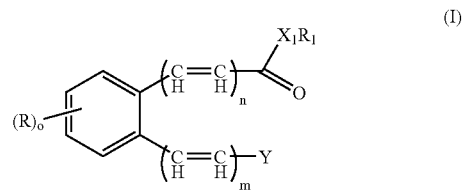

in which Y, R, $R_2$, $R_3$, $R_4$, X, $X_2$, $X_3$, n, m and o are as defined in the specification, which are formed by the microorganism *Actinomycetales* sp. DSM 14865 during its fermentation, to chemical derivatives of the serpentemycins, to a process for preparing them, and to their use as pharmaceuticals, in particular for the treatment and prophylaxis of infectious bacterial diseases.

19 Claims, No Drawings

POLYENECARBOXYLIC ACID DERIVATIVES, PROCESSES FOR PREPARING THEM, AND THEIR USE

CROSS-REFERENCE TO RELATED APPLICATION

This application claims the benefit of priority from German Patent Application No. 10229713.4, filed Jul. 2, 2002, as well as the benefit of U.S. Provisional Application No. 60/423,473, filed Nov. 4, 2002.

SUMMARY OF THE INVENTION

Compounds of formula (I)

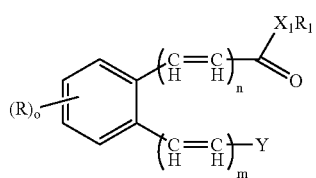

are very good inhibitors of glycosyltransferase and very effective antibacterial compounds.

BACKGROUND OF THE INVENTION

A large number of antibiotics are used therapeutically for treating infectious bacterial diseases. However, the pathogens are becoming increasingly resistant to the pharmaceuticals employed, and there is even the threat of a serious risk due to what are termed multiresistant organisms, which have not only become capable of resisting single antibiotic groups, such as β-lactam antibiotics, glycopeptides or macrolides, but also carry several resistances at one and the same time. There are even pathogens which have become resistant to all the commercially available antibiotics. Infectious diseases that are caused by these organisms can no longer be treated. There is, therefore, a great need for novel agents which can be used against resistant organisms. While thousands of antibiotics have been described in the literature, most of them are too toxic to be used as pharmaceuticals.

A relatively large number of polyene antibiotics, most of which are macrolides, that is their structures belong to the macrocyclic structure type, have already been described. These macrolides act antimycotically by means of interactions with biological membranes, and are, therefore, toxic to warm-blooded animals (homeotherms). The most important representative of this antibiotic type is amphotericin B, which is used as a therapeutic agent in humans despite its toxicity. An example of a nonmacrocyclic polyene antibiotic which has been described (Ritzau et al., Liebigs Ann. Chem. 1993, 433-435) is serpentene, which contains a phenyl ring which is substituted in the 1,2 position by polyene side chains. In tests directed against Gram-positive and Gram-negative bacteria, serpentene only exhibited a weak antibiotic effect against *Bacillus subtilis*.

The cell wall of Gram-positive bacteria is composed, inter alia, of murein, which is composed of N-acetyl-D-glucosamine and N-acetylmuramic acid, which are linked to each other like a disaccharide, and contains amino acids and peptides, such as D-glutamine, D- and L-alanine, L-lysine and pentaglycyl units, and which is strongly cross-linked. The biosynthesis of the bacterial cell wall takes place using enzymes which are not found in homeotherm metabolism. These enzymes are, therefore, suitable sites of attack for developing antibiotics which are well tolerated by homeotherms. Furthermore, inhibitors of murein biosynthesis should not be poisonous to humans. Glycosyltransferase (Transglycosylase, GT) is a key enzyme in peptidoglycan biosynthesis and, consequently, of cell wall construction. A specific inhibitor of this enzyme, i.e. moenomycin (Kurz et al., Eur. J. Biochem. 1998, 252, 500-507), has been known for a relatively long time. Moenomycin is an antibiotic which exhibits very powerful activity and which is well tolerated; however, it is not absorbed from the gastrointestinal tract, and elimination from the blood following intravenous administration is also difficult. For these reasons, it has thus far not been possible to use moenomycin systemically in medicine. Further, only a very few additional glycosyltransferase inhibitors have been described in the literature; for reasons of pharmacokinetics or tolerance, none of these agents has found its way into therapy. For this reason, novel GT inhibitors are still being sought, as has recently been reported by Goldman & Gange in Current Medicinal Chem. 2000, 7, 801-820. Screening for GT inhibitors employs specific biochemical GT test systems; such assays have been described repeatedly, for example, by Vollmer & Höltje in Antimicrobial Agents and Chemotherapy 2000, 44, 1181-1185.

Darby et al. (J. Org. Chem. 1977, 42, 1960-1967) describe the synthesis of phenyl compounds which are substituted by trans-polyene side chains in the 1,2 position for analyzing the π system of macrocyclic annulenes.

DETAILED DESCRIPTION OF THE INVENTION

It has been found, surprisingly, that the strain *Actinomycetales* sp. DSM 14865 is able to form novel compounds which are very good inhibitors of glycosyltransferase and very effective antibacterial compounds.

The invention consequently relates to the active compounds which are formed by the strain *Actinomycetales* sp. DSM 14865, and to their physiologically tolerated salts, esters, ethers and obvious chemical equivalents thereof.

The invention therefore relates to compounds of formula (I)

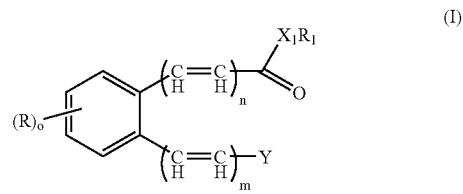

wherein:

Y is a group of formula (II)

or of formula (III)

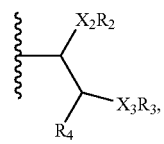

R is

H, $C_1$-$C_6$-alkyl, $C_2$-$C_6$-alkenyl, $C_2$-$C_6$-alkynyl, $C_6$-$C_{14}$-aryl, halogen, —CN, —OH, —O—$C_1$-$C_6$-alkyl, —O—$C_2$-$C_6$-alkenyl, —O—$C_6$-$C_{14}$-aryl, —O—$C_2$-$C_6$-alkynyl, —$NH_2$, —NH—$C_1$-$C_6$-alkyl, —NH—$C_2$-$C_6$-alkenyl, —NH—$C_2$-$C_6$-alkynyl, —NH—$C_6$-$C_{14}$-aryl, —N(—$C_1$-$C_6$-alkyl)$_2$, —N(—$C_2$-$C_6$-alkenyl)$_2$, —N(—$C_2$-$C_6$-alkynyl)$_2$, —N($C_6$-$C_{14}$-aryl)$_2$, —NH[—C(=O)—($C_1$-$C_6$-alkyl)], —NH[—C(=O)—($C_{6-C14}$-aryl)], —NH—O—$R_1$, —SH, —S—$C_1$-$C_6$-alkyl, —S—$C_2$-$C_6$-alkenyl, —S—$C_1$-$C_6$-alkynyl and —O—$C_6$-$C_{14}$-aryl, wherein the above-mentioned substituents can be unsubstituted or substituted, one or more times, by a substituent independently selected from $C_1$-$C_6$-alkyl, $C_2$-$C_6$-alkenyl, $C_2$-$C_6$-alkynyl, $C_6$-$C_{14}$-aryl, where alkyl, alkenyl, alkynyl and aryl may, in turn, be independently unsubstituted or substituted, once or twice, by a substituent independently selected from —OH, =O, —O—$C_1$-$C_6$-alkyl, —O—$C_2$-$C_6$-alkenyl, —O—$C_6$-$C_{14}$-aryl, —$C_6$-$C_{14}$-aryl, —NH—$C_1$-$C_6$-alkyl, —NH—$C_2$-$C_6$-alkenyl, —$NH_2$, and halogen, wherein said alkyl, alkenyl, alkynyl and aryl can be further substituted by a —CN, amide or oxime, $R_1$, $R_2$, $R_3$ and $R_4$ are, independently of each other, H, $C_1$-$C_6$-alkyl, $C_2$-$C_6$-alkenyl, $C_2$-$C_6$-alkynyl or $C_5$-$C_{14}$-aryl, in which alkyl, alkenyl, alkynyl and aryl are unsubstituted or substituted, once or twice, by a substituent independently selected from —OH, —O—$C_1$-$C_6$-alkyl, —O—$C_2$-$C_6$-alkenyl, —O—$C_6$-$C_{14}$-aryl, —$C_6$-$C_{14}$-aryl, —NH—$C_1$-$C_6$-alkyl, —NH—$C_2$-$C_6$-alkenyl, —$NH_2$ and halogen, in which alkyl, alkenyl, alkynyl and aryl are independently unsubstituted or substituted, once or twice, by a substituent independently selected from —OH, =O, —O—$C_1$-$C_6$-alkyl, —O—$C_2$-$C_6$-alkenyl, —O—$C_6$-$C_{14}$-aryl, —$C_6$-$C_{14}$-aryl, —NH—$C_1$-$C_6$-alkyl, —NH—$C_2$-$C_6$-alkenyl, —$NH_2$ and halogen, in which said alkyl, alkenyl, alkynyl and aryl can be further independently substituted by a —CN, amide or oxime, $X_1$, $X_2$ and $X_3$ are, independently of each other, selected from —$CH_2$—, —CHR—, —NH—, —N($C_1$-$C_6$-alkyl)-, —N($C_2$-$C_6$-alkenyl)-, —N($C_2$-$C_6$-alkynyl)-, —N[—C(=O)—($C_1$-$C_6$-alkyl)]-, —N[—C(=O)—($C_6$-$C_{14}$-aryl)]-, —N($C_6$-$C_{14}$-aryl)-, —N(OR)—, —O— and —S—, n and m are, independently of each other, 2, 3, 4 or 5, and o is 0, 1, 2 or 3, excluding, however, compounds of formula (I) in which o is 0, n is 2, m is 2 or 3, $X_2$ and $X_3$ are O, and $R_2$ and $R_3$ are $C_2H_5$, and all double bonds possess the trans-configuration, and/or stereoisomeric forms of compounds of formula (I) and/or a mixture of these forms in any ratio, and/or physiologically tolerated salts of compounds of formula (I).

In the foregoing definition:

$C_1$-$C_6$-Alkyl is a straight-chain or branched alkyl group having from 1 to 6 C atoms, preferably having from 1 to 4 C atoms, such as methyl, ethyl, i-propyl, tert-butyl and hexyl; $C_2$-$C_6$-Alkenyl is a straight-chain or branched alkenyl group having from 2 to 6 C atoms which is unsaturated once, twice or three times, such as allyl, crotyl, 1-propenyl, penta-1,3-dienyl and pentenyl;

$C_2$-$C_6$-Alkynyl is a straight-chain or branched alkynyl group having from 2 to 6 C atoms which is unsaturated once or twice, such as propinyl, butinyl and pentinyl;

$C_6$-$C_{14}$-Aryl is an aryl group having from 6 to 14 C atoms, such as phenyl or 1-naphthyl or 2-naphthyl, which is unsubstituted or substituted by halogen, $C_1$-$C_6$-alkyl, preferably $C_1$-$C_4$-alkyl, for example methyl, hydroxyl, —O—$C_1$-$C_6$-alkyl, preferably —O—$C_1$-$C_4$-alkyl, for example methoxy, or trifluoromethyl;

Aliphatic acyl groups —N[—C(=O)—($C_1$-$C_6$-alkyl)]- preferably contain a $C_1$-$C_4$-alkyl, for example, formyl, acetyl, propionyl, butyryl, hexanoyl, acryloyl, crotonoyl or propioloyl, and can be further substituted by halogen, e.g. chlorine, bromine or fluorine, by $NH_2$, and/or by —NH($C_1$-$C_6$-alkyl), preferably —NH($C_1$-$C_4$-alkyl), for example, methylamino or ethylamino.

Aromatic acyl —N[—C(=O)—($C_5$-$C_{14}$-aryl)]- is, for example, N-benzoyl or N-naphthoyl and can be further substituted by halogen, such as chlorine, bromine or fluorine, by $C_1$-$C_6$-alkyl, preferably $C_1$-$C_4$-alkyl, for example methyl, by hydroxyl, by —NH($C_1$-$C_6$-alkyl), preferably —NH($C_1$-$C_4$-alkyl), for example methylamino or ethylamino, or —O—$C_1$-$C_6$-alkyl, preferably —O—$C_1$-$C_4$-alkyl, for example methoxy;

Halogen is an element in the 7th main group of the periodic system, preferably chlorine, bromine or fluorine.

Unless otherwise indicated, the configuration of the double bonds in the polyene groups of the compounds of formula (I) can be in the cis or in the trans configuration. The invention relates both to the pure compounds and to stereoisomeric mixtures, such as enantiomeric mixtures and diasteromeric mixtures, in any ratio. Stereoisomeric forms are understood, in particular, as being compounds having different spatial arrangements (configurations) of the atoms or atom groups in a molecule while the atoms are linked in the same way, for example cis-trans isomers at double bonds. Preferably, at least one polyene group in a compound of formula (I) contains at least one cis double bond.

R is preferably H.

$R_1$, $R_2$, $R_3$ and $R_4$ are preferably, independently of each other, H or $C_1$-$C_6$-alkyl.

$X_1$, $X_2$ and $X_3$ are preferably, independently of each other, —O—.

m is preferably 3 or 4.

n is preferably 2.

o is preferably 0.

The general definitions of the radicals and the preferred definitions of the radicals are, R, $R_1$, $R_2$, $R_3$ and $R_4$, $X_1$, $X_2$ and $X_3$, m, n and o in the compounds of the formula (I) can, independently of each other, be combined with each other at will.

Preferred compounds of formula (I), are those wherein:

R is H, $R_1$ is H or $C_1$-$C_6$-alkyl, $R_2$ is H or $C_1$-$C_6$-alkyl, $R_3$ is H or $C_1$-$C_6$-alkyl, $R_4$ is $C_1$-$C_6$-alkyl, and $X_1$ and $X_2$ are —O—, and the physiologically tolerated salts thereof.

Also, preferred compounds of formula (I) are compounds of formula (IV)

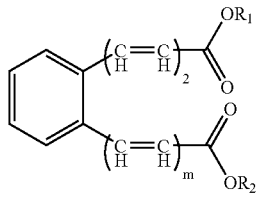

wherein m is 3 or 4, and $R_1$ and $R_2$ are as defined above for formula I, and the physiologically tolerated salts thereof. Particularly preferred are compounds of formula (IV) in which m is 4 and in which the configuration of the polyenes corresponds to formula (V):

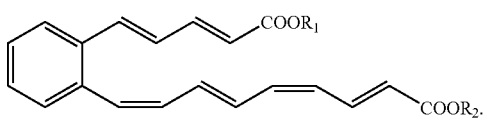

Special preference is given to the compound of the formula (V) in which $R_1$ and $R_2$ are H. This compound is referred to below as: serpentemycin A (empirical formula: $C_{20}H_{18}O_4$; MW=322.36).

Also particularly preferred are compounds of formula (IV) in which n is 2 and m is 3 and in which the configuration of the polyenes corresponds to formula (VI):

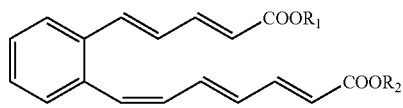

Special preference is given to the compound of formula (VI) in which $R_1$ and $R_2$ are both H. This compound is referred to below as serpentemycin B (empirical formula: $C_{18}H_{16}O_4$; MW=296.33).

Also particularly preferred are compounds of formula (IV) in which n is 2 and m is 3 and in which the configuration of the polyenes corresponds to the formula (VII):

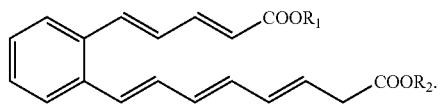

Special preference is given to the compound of the formula (VII) in which $R_1$ and $R_2$ are both H. This compound is referred to below as serpentemycin C (empirical formula: $C_{18}H_{16}O_4$; MW=296.33).

Also particularly preferred compounds of formula (I) are compounds of formula (VIII)

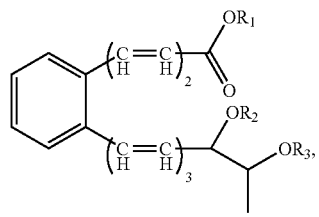

wherein $R_1$, $R_2$ and $R_3$ are as defined for formula I, and the physiologically tolerated salts thereof.

Also preferred are compounds of formula (VIII) in which $R_2$ and $R_3$ are both H and in which the configuration of the polyenes corresponds to the (IX):

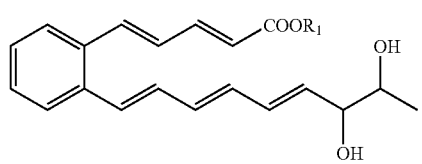

Special preference is given to the compound of the formula (IX) in which $R_1$ is H. This compound is referred to below as serpentemycin D (empirical formula: $C_{20}H_{22}O_4$; MW=236.40).

Particular preference is also given to compounds of formula (VIII) in which $R_2$ and $R_3$ are both H and in which the configuration of the polyenes corresponds to formula (X):

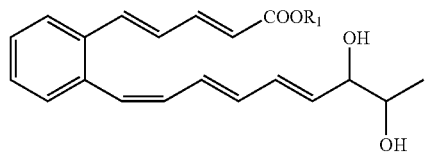

Special preference is given to the compound of formula (X) in which $R_1$ is H. This compound is referred to below as serpentemycin E.

The invention also is directed to certain of the foregoing compounds, having the empirical formula $C_{20}H_{18}O_4$ (serpentemycin A), $C_{18}H_{16}O_4$ (serpentemycin B and C) or $C_{20}H_{22}O_4$ (serpentemycin D), when obtained by fermenting *Actinomycetales* sp. DSM 14865, or one of its variants and/or mutants, in a culture medium until said compounds, serpentemycin A, B, C and/or D, accrue in the culture solution and by subsequently isolating said compound; and (1), where appropriate, converting said compound into a pharmacologically tolerated salt or (2), where appropriate, converting said compound into a chemical derivative thereof and (3), where appropriate, converting said derivative into a pharmacologically tolerated salt.

The serpentemycins A, B, C and D differ from substances known from the literature in the structural formulae which are specified. While structurally related polyenecarboxylic acid derivatives are known, they differ from the compounds according to the invention in their chemical structure, in their antimicrobial and/or biochemical activity and in other physical properties. (See, e.g., Table 1, infra.)

The invention furthermore is directed to a process for preparing compounds of formula (I), which process comprises:
1. culturirig the microorganism *Actnomycetales* sp. DSM 14865, or one of its variants and/or mutants, in an aqueous nutrient medium until one or more of the compounds serpentemycin A, B, C and D accrues in the culture broth,
2. isolating and purifying said serpentemycin A, B, C and/or D,
3. where appropriate, using a suitable reagent to convert said serpentemycin A, B, C or D into another compound of formula (I), and
4. where appropriate, converting said compound of formula (I) into a pharmacologically tolerated salt.

Examples of suitable reagents are alkylating agents, which can be used to convert carboxyl groups of the serpentemycins A, B, C and D into the corresponding ester. Examples of suitable alkylating agents are methyl iodide, diethyl sulfate, diazomethane and other alkyl derivatives as has been described, for example, by Jerry March in Advanced Organic Chemistry, John Wiley & Sons, 4$^{th}$ Edition, 1992. Double bonds can, for example, be isomerized photochemically or in the added presence of a free radical initiator. In order to carry out reactions selectively, it may be advantageous to introduce suitable protecting groups, in a manner known per se, prior to the reaction. The protecting groups are removed after the reaction, and the reaction product is then purified.

In addition to this, the invention relates to obvious chemical equivalents of the compounds of formula (I). Obvious chemical equivalents are compounds that exhibit a slight chemical difference, that is have the same activity or are converted into compounds according to the invention under mild conditions. Said equivalents include, for example, esters, amides, hydrazides, anhydrides, hydrogenation products, and reduction products, as well as complexes or adducts of or with the compounds of the invention.

Methods known to the skilled person can be used to convert a compound of formula (I) into the corresponding pharmacologically tolerated salts. Pharmacologically tolerated salts of compounds of the invention are understood as meaning both inorganic and organic salts, as are described in Remingtons Pharmaceutical Sciences (17th Edition, page 1418 [1985]). Particularly suitable salts are alkali metal, ammonium or alkaline earth metal salts, salts of physiologically tolerated amines and salts of inorganic or organic acids, such as HCI, HBr, $H_2SO_4$, maleic acid and fumaric acid.

The strain *Actnomycetales* sp. DSM 14865 forms the compounds Serpentemycins A, B, C and D on nutrient solutions which contain glucose, starch, yeast extract or glycerol.

In addition to this, *Actnomycetales* sp. DSM 14865 forms numerous by-products possessing slightly varying polyene chains.

An isolate of *Actnomycetales* sp. was deposited in the Deutsche Sammlung von Mikroorganismen und Zellkulturen GmbH (DSM) [German collection of microorganisms and cell cultures], Mascheroder Weg 1B, 38124 Brunswick, Germany, on Mar. 18, 2002 under the number DSM 14865, in accordance with the rules of the Budapest treaty.

On oat-flake medium, *Actinomycetales* sp. DSM 14865 possesses a brown-beige substrate mycelium and a sparse aerial mycelium. In culture, it does not form any of the fruiting bodies which are characteristic of the *Actinomycetes*.

The foregoing synthesis process comprises culturing *Actnomycetales* sp. DSM 14865, its mutants and/or variants, under aerobic conditions in culture media that contain a carbon and nitrogen source, inorganic salts and, where appropriate, trace elements.

Instead of the strain *Actnomycetales* sp. DSM 14865, it is also possible to use its mutants and variants, provided that they synthesize the compounds of the invention.

A mutant is a microorganism in which one or more genes in the genome have been modified, with the gene or genes which is/are responsible for the ability of the organism to produce the inventive compound being retained such that it/they is/are functional and heritable.

Such mutants can be produced, in a manner known per se, by physical means, for example irradiation, such as using ultraviolet rays or X-rays, or by using chemical mutagens, such as ethyl methanesulfonate (EMS); 2-hydroxy-4-methoxybenzophenone (MOB) or N-methyl-N'-nitro-N-nitrosoguanidine (MNNG), or as described by Brock et al. in "Biology of Microorganisms", Prentice Hall, pages 238-247 (1984).

A variant is a phenotype of the microorganism. Microorganisms have the ability to adapt to their environment and therefore exhibit highly developed physiological flexibility. All the cells of the microorganism are involved in the phenotypic adaptation, with the nature of the change not being conditioned genetically and being reversible under altered conditions (H. Stolp, Microbial ecology: organismus, habitats, activities. Cambridge University Press, Cambridge, GB, page 180, 1988).

The screening for mutants and variants which produce the antibiotic compounds of the invention can be effected by determining the biological activity of the active compound which has accrued in the culture broth, for example by determining its antibacterial effect, or else by detecting compounds in the fermentation broth which are known to possess antibacterial activity, for example, using HPLC or LC-MS methods.

Suitable and preferred carbon sources for the fermentation are assimilable carbohydrates and sugar alcohols, such as glucose, lactose, sucrose and D-mannitol, and also carbohydrate-containing natural products, such as malt extract and yeast extract. Suitable nitrogen sources are: amino acids, peptides and proteins and their breakdown products, such as casein, peptones or tryptones, and also meat extracts, yeast extracts, ground seeds, for example, corn, wheat, beans, soybean and the cotton plant, distillation residues from alcohol production, meat meals or yeast extracts, and also ammonium salts and nitrates, in particular peptides which have been obtained synthetically or biosynthetically. Examples of inorganic salts and trace elements which the nutrient solution can contain are chlorides, carbonates, sulfates and phosphates of the alkali metals or alkaline earth metals, iron, zinc, cobalt and manganese.

The formation of the compounds of the invention proceeds particularly well, for example, in a nutrient solution which contains about 0.05 to 5%, preferably from 0.5 to 2%, of starch, from 0.05 to 3%, preferably from 0.1 to 1%, of yeast extract, from 0.05 to 5%, preferably from 0.1 to 2%, of glucose, from 0.2 to 5%, preferably from 0.5% to 2%, of glycerol, from 0.05 to 3%, preferably from 0.1 to 1%, of Consteep, from 0.05 to 3%, preferably from 0.1 to 1%, of peptone, from 0.05 to 3%, preferably from 0.05 to 0.5%, of NaCl and from 0.05 to 3%, preferably from 0.1 to 1%, of $CaCO_3$. The percentage values are in each case based on the weight of the entire nutrient solution.

In the nutrient solution, *Actnomycetales* sp. DSM 14865 forms a mixture of the serpentemycins A, B, C and D and byproducts. The quantitative proportion of one or more of the compounds according to the invention can vary, depending on the composition of the nutrient solution. In addition, the synthesis of individual polyenecarboxylic acids can be controlled by the composition of the medium such that the microorganism does not produce an antibiotic at all or produces it in a quantity that is below the detection limit.

The microorganism is cultured aerobically, that is, for example, submerged while being shaken or stirred in shaking flasks or fermenters, or on solid medium, where appropriate, while passing in air or oxygen. The culture can be carried out in a temperature range of from about 15 to 35° C., preferably at from about 25 to 32° C., particularly at from 27 to 30° C. The pH range should be between 4 and 10, preferably between 6.5 and 7.5. The microorganism is generally cultured under these conditions over a period of from 48 to 720 hours, preferably from 72 to 320 hours, advantageously in several steps; i.e. one or more preliminary cultures are initially prepared in a liquid nutrient medium, with these preliminary cultures then being inoculated, for example in a volume ratio from 1:10 to 1:100, into the actual production medium, i.e. the main culture. The preliminary culture is obtained, for example, by inoculating the mycelium into a nutrient solution, and allowing it to grow for from about 20 to 120 hours, preferably from 48 to 72 hours. The mycelium can be obtained, for example, by allowing the strain to grow for from about 1 to 40 days, preferably from 14 to 21 days, on a solid or liquid culture medium, for example yeast-malt-glucose agar, oat flake agar or starch agar.

The course of the fermentation, and the formation of the antibiotics according to the invention, can be monitored using methods which are known to a person skilled in the art, for example by means of testing the biological activity in bioassays or by means of chromatographic methods such as thin layer chromatography (TLC) or high performance liquid chromatography (HPLC).

*Actnomycetales* sp. DSM 14865 is able to form compounds of the invention by means of submerged fermentation. The compounds according to the invention can be present both in the mycelium and in the culture filtrate; the major quantity is usually present in the culture filtrate. It is therefore expedient to separate off the fermentation solution by filtration or centrifugation. The filtrate is extracted using an adsorption resin as a solid phase. The mycelium, and also the surface culture, is expediently extracted with a suitable solvent, for example methanol or 2-propanol.

While the extraction can be carried out in a broad pH range, it is expedient to carry it out in a neutral or weakly acidic medium, preferably between pH 3 and pH 7. The extracts can, for example, be concentrated in vacuo and dried.

One method of isolating the antibiotic compounds of the invention is solution partition, carried out in a manner known per se.

Another purification method is that of chromatography on adsorption resins, such as Diaion® HP-20 (Mitsubishi Casei Corp., Tokyo, Japan), Amberlite® XAD 7 (Rohm and Haas, USA), Amberchrom® CG (Toso Haas, Philadelphia, USA) and the like. In addition, a large number of reverse phase supports, e.g. $RP_8$ and $RP_{18}$, as have become wellknown, for example, within the context of high pressure liquid chromatography (HPLC), are also suitable.

Another option for purifying the antibiotic compounds of the invention is the use of 'normal phase chromatography supports', such as silica gel, $Al_2O_3$, or others, in a manner known per se.

An alternative isolation method is that the use of molecular sieves such as Fractogel® TSK HW-40 (Merck KGaA, Darmstadt, Germany), Sephadex® G-25 (Amersham Biosciences, Uppsala, Sweden) and others, in a manner known per se. In addition, it is also possible to obtain the novel polyenecarboxylic acids by crystallizing them from concentrated solutions. Organic solvents and their mixtures, either with or without water, or various salts, are, for example, suitable for this purpose. An additional method for isolating and purifying the antibiotic compounds of the invention is that the use of anion exchangers, preferably in a pH range from 4 to 10. The use of buffer solutions to which quantities of organic solvents have been added is particularly suitable for this purpose.

It has been found, surprisingly, that the compounds of the invention are powerful inhibitors of glycosyltransferase. Selective and powerful inhibitors of glycosyltransferase, such as the antibiotics of the moenomycin group, always exhibit antibacterial effects, with a low inhibitory concentration ($IC_{50}$) being associated with powerful bacteriostatic activity. The compounds of the invention possess bacteriostatic activity because they inhibit the growth and replication of the bacteria; they are therefore suitable for treating diseases that are caused by bacterial infections. Table 1 summarizes, by way of example, the inhibitory concentrations ($IC_{50}$) of some compounds of the invention. A special test system was used for finding glycosyltransferase inhibitors that are specific and very effective. This system uses a glycosyltransferase/$^3$H-moenomycin complex, which is brought into contact with substances that are to be tested. The determination of the GT-inhibitory effect is based on the displacement of radioactively labeled moenomycin A from the glycosyltransferase (PBP 1b)/$^3$H-moenomycin complex, it being possible to separate the released $^3$H-moenomycin, as a soluble compound, from the fixed complex and to measure the remaining radioactivity using a Geiger counter.

TABLE 1

The inhibitory constants ($IC_{50}$ values) of the antibiotic compounds of the invention in the glycosyltransferase assay.

| | |
|---|---|
| serpentemycin A: | 0.2 µM |
| serpentemycin B: | 0.1 µM |
| serpentemycin C: | 21 µM |
| serpentemycin D: | 19 µM |

The inhibitory constant of serpentene (Ritzau et al., Liebigs Ann. Chem. 1993, 433-435) was determined for comparison: the $IC_{50}$ value was 18 µM.

The present invention consequently also relates to the use of a compound of the formula (I) as a pharmaceutical, preferably for the treatment and/or prophylaxis of bacterial infections.

The invention also relates to the use of a compound of formula (I) for the treatment and/or prophylaxis of bacterial infections.

In addition, the present invention relates to a pharmaceutical composition containing one or more of the compounds of the invention.

The pharmaceutical composition is produced by mixing at least one compound of formula (I) with one or more physiologically suitable auxiliary substances and modifying this mixture into a suitable form for administration.

In general, the pharmaceutical compositions of the invention are administered orally, locally or parenterally; however, it is also possible in principle to use them rectally. Examples of suitable solid or liquid galenic preparation forms are granules, powders, tablets, sugar-coated tablets, microcapsules, suppositories, syrups, emulsions, suspensions, aerosols, drops or injectable solutions in ampoule form, and also preparations that provide a protracted release of active compound, in the production of which physiologically suitable adjuvants such as disintegrants, binding agents, coating agents, swelling agents, glidants, lubricants, flavorings, sweeteners and solubilizers are customarily used. Examples of frequently employed auxiliary substances include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols.

Where appropriate, the dosage units for oral administration can be microencapsulated in order to delay release or extend it over a relatively long period of time, for example by means of coating or embedding the active compound, in particle form, in suitable polymers, waxes or the like.

In general, a suitable dose is in the range from 0.1 to 1000, preferably from 0.2 to 100, mg/kg of bodyweight. These amounts are expediently administered in dosage units that at least contain the effective daily quantity of the compounds of the invention, e.g. 30-3000, preferably 50-1000, mg.

The following examples are intended to clarify the invention without in any way limiting its scope.

EXAMPLE 1

Preparing a Glycerol Culture of *Actnomycetales* sp. DSM 14865

30 ml of nutrient solution (malt extract 1.0%, yeast extract 0.4%, glucose, 0.4%, pH 7.0 in water) were inoculated, in a sterile 100 ml Erlenmeyer flask, with the strain *Actinomycetales* sp, DSM 14865 and incubated for 7 days at 28° C. and 180 rpm on a rotating shaker. In each case, 1.5 ml of this culture were then diluted with 2.5 ml of 80% glycerol and stored at −135° C.

EXAMPLE 2

Preparing a Preliminary Culture of *Actnomycetales* sp, DSM 14865 in an Erlenmeyer Flask In each case, 100 ml of nutrient solution (glucose 1.5%, soybean meal, 1.5%, Cornsteep, 0.5%, $CaCO_3$, 0.2% and NaCl, 0.5%, pH 7.0) were inoculated, in a sterile 300 ml Erlenmeyer flask, with the strain *Actnomycetales* sp, DSM 14865 and incubated for 4 days, at 28° C. and 180 rpm, on a rotating shaker. This preliminary culture was then used for inoculating the main cultures.

EXAMPLE 3

Kinetics of the Formation of the Aromatic Polyenecarboxylic Acids in the Shaken Cultures of *Actnomycetales* sp, DSM 14865

Cultures of *Actnomycetales* sp, DSM 14865 were started, as described in Example 2, in 20 Erlenmeyer flasks, and the cultures were incubated on a shaker for a period of up to 2 weeks. Shaking flasks were removed after 48, 72, 96, 102, 120, 240 and 312 hours. After the mycelium was separated off, and after the solid-phase extraction of the aromatic polyenecarboxylic acids from the culture filtrate with MCI-Gel® (Mitsubishi Chemical Industries) and elution with methanol, the extracts were analyzed by HPLC as described in Example 8. The changes in the HPLC surface area units, which occurred as a function of the incubation time, are listed in the following table. The surface area units are proportional to the concentrations of the products.

TABLE 2

Change in the concentrations of the products occurring over the time during which Actinomycetales sp, DSM 14865 is incubated in shaken cultures. The product concentrations are proportional to the given HPLC surface area units.

| Incubation time | Serpentemycins | | | | Serpentene |
|---|---|---|---|---|---|
| | A | B | C | D | |
| 48 h | 174 | 132 | 151 | 54 | 574 |
| 72 h | 313 | 284 | 372 | 94 | 1948 |
| 96 h | 727 | 443 | 891 | 242 | 2530 |
| 102 h | 698 | 424 | 814 | 358 | 1878 |
| 120 h | 816 | 470 | 1098 | 430 | 1212 |
| 240 h | 917 | 1216 | 1786 | 1437 | 47 |
| 312 h | 882 | 1411 | 1877 | 734 | 35 |

Whereas serpentene has already reached its maximum formation after 96 hours, the highest concentrations of serpentemycins A and D are only to be observed after 10 days. The products serpentemycin B and C are even present at their highest concentrations after 13 days.

EXAMPLE 4

Fermenting *Actnomycetales* sp. DSM 14865 in Order to Produce Serpentemycin A In order to produce the antibioticcompounds of the invention, the strain *Actnomycetales* sp. DSM 14865 was fermented in 30 L fermenters. The nutrient solution employed was the following: 10 g of soluble starch/L; 10 g of glucose/L; 10 g of glycerol/L; 2.5 g of Cornsteep, liquid/L; 5 g of peptone/L; 2 g of yeast extract/L; 1 g of NaCl/L; 3 g of $CaCO_3$/L (in water); pH prior to sterilization, 7.2. Good growth and rapid productivity were observed in this nutrient medium. The fermentation was carried out under the following conditions:

Sterilization: in-situ, 20 min at T = 121° C.
Inoculum: 6%
Stirring speed: 180 rpm
T: 28° C.
Air: 0.45 $m^3$/h
$pO_2$: not regulated
pH, during fermentation: about 6.2; not regulated.

Under these conditions, good growth was seen within the first 70 h; at this time, the Carbon source in the medium had been consumed and growth was stagnating. After 80 h, it was possible to detect the first formation of of the compounds of the invention. The fermenters were harvested after 98 h.

EXAMPLE 5

Isolating Serpentemycin A from the *Actnomycetales* sp. DSM 14865 Culture Solution After the fermentation of *Actnomycetales* sp. DSM 14865 had come to an end, 27.5 liters of culture broth from the fermenter, obtained as described in Example 4, were filtered in the added presence of approx. 2% of filtration accelerator (Celite®), and the resulting cell mass (1890 g) was extracted with 6 liters of methanol. The active compound-containing, methanolic solution was freed from the mycelium by filtration and concentrated in vacuo. The concentrate was combined with 25 L of the culture filtrate, after which the pH was adjusted to 7, and the resulting combination was then loaded onto a previously prepared 3 liter ®MCI GEL, CHP20P column. The column was eluted with a gradient of 50 mM $NH_4$ acetate buffer in water after purging with 2-propanol. The column flow-through (7 liters per hour) was collected in fractions (in each case 2 liters) and the antibiotic compound-containing fractions 4 to 11 and 16 to 19 were, in each case, combined and concentrated in vacuo. The fractions were analyzed using HPLC. Fractions 4 to 11 contained the more polar serpentemycins, while fractions 16 to 19 contained the serpentenes. The serpentene-containing fractions were purified twice chromatographically on LiChrospher® 100 RP-18e, 250×25 mm, HPLC columns first using 50 mM $NH_4$ acetate buffer/acetonitrile mixtures and then using 0.05% trifluoroacetic acid/acetonitrile gradients. Freeze-drying the fractions containing pure antibiotic compound resulted in 19 mg of pure serpentene.

After they had been concentrated in vacuo, the more polar compounds in fractions 4 to 11 were purified once again by column chromatography on 160 mL MCI GEL® CHP20P (column dimensions: 26 mm×300 mm) using a gradient method. The gradient ranged from 10% to 60% acetonitrile in 50 mM $NH_4$ acetate buffer over 2 hours. The column flow-through was 25 mL per minute, while the fraction size was 50 mL. The compounds serpentemycin B and D were located in fractions 15 to 35, while fractions 36 to 39 contained serpentemycin C and fractions 40 to 43 contained serpentemycin A. The latter (fractions 40-43) were freed from organic solvent in vacuo, after which 0.01% ascorbic acid was added, and purification by isocratic chromatography was carried out on a LiChrospher® 100 RP-18e, 250-25, HPLC column using 45% acetonitrile in 0.05% trifluoroacetic acid. The fractions which contained pure serpentemycin A (fractions 31 to 35) were freeze-dried in the dark, and the serpentemycin A was stored, air-tight, in an argon atmosphere (37 mg). ESI⁻ mass spectrometry: 321.4 (M–H), ESI⁺ mass spectrometry: 305.3 (MH–$H_2O$). UV maxima: 315 and 355 nm. The NMR data are listed in Table 3, with the C atoms being numbered as follows:

TABLE 3

NMR-chemical shifts of serpentemycin A in DMSO at 300° K.

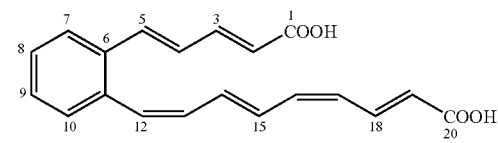

| C number | ¹H | ¹³C |
|---|---|---|
| 1 | — | 167.43 |
| 2 | 6.02 | 122.54 |
| 3 | 7.35 | 144.35 |
| 4 | 7.04 | 128.09 |
| 5 | 7.19 | 137.16 |
| 6 | — | 134.33 |
| 7 | 7.73 | 125.93 |
| 8 | 7.35 | 127.90 |
| 9 | 7.35 | 128.57 |

TABLE 3-continued

NMR-chemical shifts of serpentemycin A in DMSO at 300° K.

| C number | ¹H | ¹³C |
|---|---|---|
| 10 | 7.27 | 130.22 |
| 11 | — | 135.78 |
| 12 | 6.81 | 130.33 |
| 13 | 6.63 | 131.24 |
| 14 | 6.59 | 132.61 |
| 15 | 7.15 | 130.33 |
| 16 | 6.41 | 136.57 |
| 17 | 6.21 | 127.45 |
| 18 | 7.70 | 138.40 |
| 19 | 5.95 | 123.07 |
| 20 | — | 167.48 |

Serpentemycin A:

Appearance: lemon-yellow substance which is soluble in medium-polar and polar organic solvents and not particularly soluble in water; stable in neutral and mildly acidic media but unstable in strongly acidic and strongly alkaline solution.

Serpentemycin A is sensitive to light and air.

Empirical formula: $C_{20}H_{18}O_4$

Molecular weight: 322.36

EXAMPLE 6

Isolating and Describing Serpentemycin B

The serpentemycin B-containing fractions 36 to 39 from the 160 mL MCI GEL® CHP20P column, obtained as described in Example 4, were concentrated in vacuo, and the aqueous solution, which still contained a little acetonitrile, was loaded onto a LiChrospher® 100 RP-18e, 250-25, HPLC column. The column was eluted isocratically, using 42% acetonitrile in 0.05% trifluoroacetic acid (pH 2.4). The column flow through was 39 mL/minute; fractions were removed every 19.5 mL and analyzed by HPLC. Fractions 22 to 24 contained the antibiotic compound serpentemycin B; they were rechromatographed on the same column with the acetonitrile concentration in the eluent having been reduced to 40%. Fractions 38 to 42 contained pure serpentemycin B; they were freeze-dried, and yielded 10.2 mg of the antibiotic compound. ESI⁻ mass spectrometry: 295.0985 (M–H), ESI⁺ mass spectrometry: 297.1164 (M+H), corresponding to the empirical formula $C_{18}H_{16}O_4$. UV maxima: 306 and 332 nm in acetonitrile/0.1% phosphoric acid in water. The NMR data are listed in Table 4; the numbering of the atoms is analogous to the serpentemycin A numbering.

TABLE 4

NMR-chemical shifts of serpentemycin B in DMSO at 300° K.

| C number | ¹H | ¹³C |
|---|---|---|
| 1 | — | 167.42 |
| 2 | 6.02 | 122.59 |
| 3 | 7.35 | 144.32 |
| 4 | 7.05 | 128.23 |

TABLE 4-continued

NMR-chemical shifts of serpentemycin B in DMSO at 300° K.

| C number | $^1$H | $^{13}$C |
|---|---|---|
| 5 | 7.19 | 137.09 |
| 6 | — | 134.40 |
| 7 | 7.74 | 126.00 |
| 8 | 7.36 | 128.10 |
| 9 | 7.36 | 128.61 |
| 10 | 7.28 | 130.31 |
| 11 | — | 135.40 |
| 12 | 6.90 | 131.86 |
| 13 | 6.53 | 130.54 |
| 14 | 6.81 | 135.71 |
| 15 | 6.65 | 132.89 |
| 16 | 7.19 | 143.79 |
| 17 | 5.93 | 122.69 |
| 18 | — | 167.33 |

Serpentemycin B:

Appearance: pale yellow substance that is soluble in medium-polar and polar organic solvents and not particularly soluble in water; stable in neutral and mildly acidic media, but unstable in strongly acidic and strongly alkaline solution.

Serpentemycin B is sensitive to light and air.

| Empirical formula: | $C_{18}H_{16}O_4$ |
|---|---|
| Molecular weight: | 296.33 |

EXAMPLE 7

Isolating and Describing Serpentemycin C 450 mg of ascorbic acid were added to 45 liters of culture filtrate, obtained as described in Example 3, and the whole was loaded, at pH 4.5, onto a 3.5 liter MCI GEL® CHP20P column (15 cm×20 cm). The column was eluted with a gradient of 0.1% $NH_4$ acetate buffer, pH 4.5, after purging with 2-propanol. The flow through was 15 liters/hour. The propanol-containing efflux was collected in fractions (in each case 7 liters); fraction 6 contained the polar aromatic polyenedicarboxylic acids. They were concentrated in vacuo, after which 50 mg of ascorbic acid were added and the pH of the aqueous solution was adjusted to 3; the solution was then loaded onto a 490 mL MCI GEL® CHP20P column (5 cm×30 cm). Desorption was carried out using a gradient of 10% acetonitrile in 0.5% acetic acid, after 100% acetonitrile, at a flow rate of 25 mL per minute; the fraction time was 10 minutes (in each case 250 mL). The polar aromatic polyenedicarboxylic acids were located in fractions 12 to 19; they were pooled, concentrated in vacuo and further purified by means of gel permeation chromatography. The support employed was 3.9 L of Fractogel® TSK HW-40 (column dimensions: 10×50 cm), while the mobile phase employed was a mixture consisting of 60% acetonitrile, 20% methanol and 20% 25 mM $NH_4$ acetate buffer, pH 7. At a flow through of 4.5 mL/minute, fractions were collected every half hour (in each case 135 mL). Fractions 37 to 40, which were examined by HPLC, contained the compound serpentemycin C. The final purification took place on LiChrospher® 100 RP-18e, 250-25 using the mobile phase 50 mM $NH_4$ acetate buffer, pH 7/acetonitrile. The fractions containing pure serpentemycin C were pooled and desalted through LiChrospher® RP-18e, 250-10, using water/acetonitrile. Freeze-drying yielded 15 mg of serpentemycin C ammonium salt. ESI$^-$ mass spectrometry: 295.1 (M−H), ESI$^+$ mass spectrometry: 279.2 (MH−H$_2$O), corresponding to the empirical formula $C_{18}H_{16}O_4$. UV maxima: 212, 308 and 356 nm in acetonitrile/0.1% phosphoric acid in water (1:1). The NMR data are listed in Table 5; the numbering of the atoms is analogous to the serpentemycin A numbering.

TABLE 5

NMR-chemical shifts of serpentemycin C in DMSO at 300° K.

| C number | $^1$H | $^{13}$C |
|---|---|---|
| 1 | — | 167.94 |
| 2 | 6.03 | 124.53 |
| 3 | 7.37 | 143.06 |
| 4 | 6.98 | 129.04 |
| 5 | 7.45 | 135.64 |
| 6 | — | 134.29 |
| 7 | 7.65 | 126.29 |
| 8 | 7.29 | 128.25 |
| 9 | 7.32 | 128.70 |
| 10 | 7.66 | 125.99 |
| 11 | — | 135.01 |
| 12 | 7.26 | 132.17 |
| 13 | 6.97 | 130.76 |
| 14 | 6.87 | 139.75 |
| 15 | 6.59 | 131.34 |
| 16 | 7.18 | 142.39 |
| 17 | 5.95 | 124.21 |
| 18 | — | 167.33 |

Serpentemycin C:

Appearance: pale yellow substance that is soluble in medium-polar and polar organic solvents and not particularly soluble in water; stable in neutral and mildly acidic medium but unstable in strongly acidic and strongly alkaline solution.

Serpentemycin C is sensitive to light and air.

| Empirical formula: | $C_{18}H_{16}O_4$ |
|---|---|
| Molecular weight: | 296.33 |

EXAMPLE 8

Isolating and Describing Serpentemycin D

The serpentemycin D-containing fractions 36 to 39 from the 160 mL MCI GEL® CHP20P column, obtained as described in Example 4, were concentrated in vacuo and the aqueous solution, which still contained a little acetonitrile, was loaded onto a LiChrospher® 100 RP-18e, 250-25, HPLC column. The column was eluted isocratically using 42% acetonitrile in 0.05% trifluoroacetic acid (pH 2.4). The column flow-through was 39 mL/minute; fractions of, in each case, 19.5 mL, were taken and analyzed by HPLC, as described in Example 9. Fractions 51 to 53 contained the antibiotic serpentemycin D; they were rechromatographed on the same column, as described, except that the concentration of acetonitrile in the eluent was reduced to 40%. Fractions 13 to 15 contained pure serpentemycin D; they were freeze-dried and yielded 3 mg of the antibiotic. ESI$^-$ mass spectrometry: 325.5 (M−H), ESI$^+$ mass spectrometry: 349.2 (M+Na), corresponding to the empirical formula $C_{20}H_{22}O_4$. UV maxima: 299 and 338 nm in acetonitrile/

0.1% phosphoric acid in water. The NMR data are listed in Table 6; the atoms were numbered in analogy with the compound serpentemycin A.

TABLE 6

NMR-chemical shifts of serpentemycin D in DMSO at 300° K.

| C number | $^1$H | $^{13}$C |
|---|---|---|
| 1 | — | 167.54 |
| 2 | 6.02 | 122.38 |
| 3 | 7.45 | 144.49 |
| 4 | 6.99 | 128.31 |
| 5 | 7.49 | 136.82 |
| 6 | — | 133.56 |
| 7 | 7.64 | 126.22 |
| 8 | 7.25 | 127.52 |
| 9 | 7.31 | 128.84 |
| 10 | 7.62 | 125.68 |
| 11 | — | 135.74 |
| 12 | 7.07 | 128.14 |
| 13 | 6.89 | 131.72 |
| 14 | 6.48 | 132.12 |
| 15 | 6.45 | 134.02 |
| 16 | 6.30 | 129.68 |
| 17 | 5.90 | 136.71 |
| 18 | 3.82 | 75.31 |
| 18-OH | 4.81 (broad) | — |
| 19 | 3.48 | 69.77 |
| 19-OH | 4.48 (broad) | — |
| 20 | 1.03 | 19.10 |

Serpentemycin D:

Appearance: pale yellow substance that is soluble in medium-polar and polar organic solvents and not particularly soluble in water. It is stable in neutral and mildly acidic media but unstable in strongly acidic and strongly alkaline solution.

Serpentemycin D is sensitive to light and air.

| Empirical formula: | $C_{20}H_{22}O_4$ |
|---|---|
| Molecular weight: | 326.40 |

EXAMPLE 9

High Pressure Liquid Chromatography (HPLC) of the Serpentemycins

HPLC was carried out under the following conditions:

| Column: | Superspher 100 RP-18e ®, 250-4, with precolumn, |
|---|---|
| Mobile phase: | 50% acetonitrile in 0.1% phosphoric acid, |
| Flow rate: | 1 mL per minute, |
| Column temperature: | 40° C., |
| Detection by means of UV absorption at 210 nm: | |

The following retention times were observed:

| Serpentemycin A | 10.1 minutes, |
|---|---|
| Serpentemycin B | 5.6 minutes, |
| Serpentemycin C | 7.3 minutes, |
| Serpentemycin D | 5.2 minutes. |

EXAMPLE 10

Determining the Inhibition of Glycosyltransferase by Serpentemycins

The assay was carried out as described by Vollmer & Höltje (Antimicrobial Agents and Chemotherapy 2000, 44, 1181-1185), except that purified penicillin-binding protein 1b (PBP 1b; 5 pM), carrying $^3$H-labeled moenomycin at the glycosyltransferase site, was used in the present example instead of [3H]benzylpenicillin. $^3$H-Moenomycin was obtained from moenomycin A (Kurz et al., Eur. J. Biochem., 1998, 252, 500-507) by hydrogenating it with $^3$H$_2$:

6 mg of moenomycin, dissolved in 300 μL methanol, were added to a 1 cm$^3$ flask, after which 2 mg of palladium-charcoal (Degussa Type E10N/D) were added. The flask was then gassed, while excluding air, with 1 cm$^3$ $^3$H$_2$; and the reaction solution was left to hydrogenate for 15 minutes. After the reaction had come to an end, the catalyst was filtered off from the reaction mixture, which was diluted to 100 mL with ethanol. This solution can be used directly for preparing the glycosyltransferase/$^3$H-moenomycin complex. Total radioactivity of the reaction product: 6.56 GBq (177 mCi); specific activity: 1.9 TBq/mmol. The radioactive complex was attached to SPA PVT Copper His-Tag beads. The radioactive moenomycin that was displaced by the inhibitors was measured.

SPA PVT Copper His-Tag beads: Amersham RPN 0095;
PBS: GIBCO BRL 14200-067;
BSA: Calbiochem 12657;
NOG: SIGMA O-8001 (n-octyl β-D-glucopyranoside);
Tween 20: Acros 23336-067;
Microtiter plates: Greiner Labortechnik.

The determination was carried out in microtiter plates. 10 μL of the test solution were added to the microtiter plates, followed by 10 μL of $^3$H-moenomycin (25 nM, 3.1 kBq/well) and 40 μL of SPA beads loaded with PBP 1b (100 μg of beads, 45 nM enzyme). The plates were sealed and left to stand at room temperature for 8 hours. After that, the beads were separated off from the test solution by centrifuging for 3 minutes at 1300 rpm. The distribution of the radioactivity was measured in a WALLAC MicroBeta® 1450 Counter.

The inhibitory values were calculated in accordance with the formula:

$$[1-(\text{cpm}_{sample}-\text{cpm}_{low\ ctr})/(\text{cpm}_{high\ ctr}-\text{cpm}_{low\ ctr})] \times 100(\%).$$

The invention claimed is:
1. A compound of formula (I)

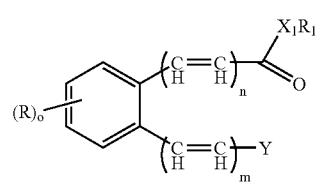

in which:
Y is a group of formula (II)

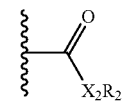

or a group of formula (III)

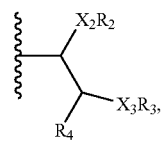

R is

H, $C_1$-$C_6$-alkyl, $C_2$-$C_6$-alkenyl, $C_2$-$C_6$-alkynyl or $C_5$-$C_{14}$-aryl, halogen, —CN, —OH, —O—$C_1$-$C_6$-alkyl, —O—$C_2$-$C_6$-alkenyl, —O—$C_5$-$C_{14}$-aryl, —O—$C_2$-$C_6$-alkynyl, —$NH_2$, —NH—$C_2$-$C_6$-alkyl, —NH—$C_2$-$C_6$-alkenyl, —NH—$C_2$-$C_6$-alkynyl, —NH—$C_5$-$C_{14}$-aryl, —N(—$C_1$-$C_6$-alkyl)$_2$, —N(—$C_2$-$C_6$-alkenyl)$_2$, —N(—$C_2$-$C_6$-alkynyl)$_2$, —N($C_5$-$C_{14}$-aryl)$_2$, —NH[—C(=O)—($C_1$-$C_6$-alkyl)], —NH[—C(=O)—($C_5$-$C_{14}$-aryl)], —NH—O—$R_1$, —SH, —S—$C_1$-$C_6$-alkyl, —S—$C_2$-$C_6$-alkenyl, —S—$C_1$-$C_6$-alkynyl or —O—$C_5$-$C_{14}$-aryl, wherein the abovementioned substituents are unsubstituted or substituted, one or more times, by a substituent independently selected from $C_1$-$C_6$-alkyl, $C_2$-$C_6$-alkenyl, $C_2$-$C_6$-alkynyl, $C_5$-$C_{14}$-aryl, where alkyl, alkenyl, alkynyl and aryl may be independently unsubstituted or substituted, once or twice, by a substituent independently selected from —OH, =O, —O—$C_1$-$C_6$-alkyl, —O—$C_2$-$C_6$-alkenyl, —O—$C_5$-$C_{14}$-aryl, —$C_5$-$C_{14}$-aryl, —NH—$C_1$-$C_6$-alkyl, —NH—$C_2$-$C_6$-alkenyl, —$NH_2$, and halogen, wherein alkyl, alkenyl, alkynyl and aryl can be further substituted by a —CN, amide or oxime, $R_1$, $R_2$, $R_3$ and $R_4$ are, independently of each other, H, $C_1$-$C_6$-alkyl, $C_2$-$C_6$-alkenyl, $C_2$-$C_6$-alkynyl or $C_5$-$C_{14}$-aryl, in which alkyl, alkenyl, alkynyl and aryl are unsubstituted or substituted, once or twice, by a substituent independently selected from —OH, —O—$C_1$-$C_6$-alkyl, —O—$C_2$-$C_6$-alkenyl, —O—$C_5$-$C_{14}$-aryl, —$C_5$-$C_{14}$-aryl, —NH—$C_1$-$C_6$-alkyl, —NH—$C_2$-$C_6$-alkenyl, —$NH_2$ and halogen, in which alkyl, alkenyl, alkynyl and aryl are independently unsubstituted or substituted, once or twice, by a substituent independently selected from —OH, =O, —O—$C_1$-$C_6$-alkyl, —O—$C_2$-$C_6$-alkenyl, —O—$C_5$-$C_{14}$-aryl, —$C_5$-$C_{14}$-aryl, —NH—$C_1$-$C_6$-alkyl, —NH—$C_2$-$C_6$-alkenyl, —$NH_2$ and halogen, in which said alkyl, alkenyl, alkynyl and aryl can be further independently substituted by a —CN, amide or oxime, $X_1$, $X_2$ and $X_3$ are, independently of each other, selected from —$CH_2$—, —CHR—, —NH—, —N($C_1$-$C_6$-alkyl)—, —N($C_2$-$C_6$-alkenyl)—, —N($C_2$-$C_6$-alkynyl)—, —N[—C(=O)—($C_1$-$C_6$-alkyl)]-, —N[—C(=O)—($C_5$-$C_{14}$-aryl)]-, —N($C_5$-$C_{14}$-aryl)—, —N(O—R)—, —O— and —S—, n and m are, independently of each other, 2, 3, 4 or 5, and o is 0, 1, 2 or 3, excluding, however, compounds of formula (I) in which o is 0, n is 2, m is 2 or 3, $X_2$ and $X_3$ are O, and $R_2$ and $R_3$ are $C_2H_5$, and all double bonds possess the trans-configuration, and/or stereoisomeric forms of compounds of formula (I) and/or a mixture of these forms in any ratio, and/or physiologically tolerated salts of compounds of formula (I).

2. A compound of formula (I) as claimed in claim 1, wherein at least one polyene group contains at least one cis double bond.

3. A compound of formula (I) as claimed in claim 1, wherein

R is H, $R_1$ is H or $C_1$-$C_6$-alkyl, $R_2$ is H or $C_1$-$C_6$-alkyl, $R_3$ is H or $C_1$-$C_6$-alkyl, $R_4$ is $C_1$-$C_6$-alkyl, and $X_1$ and $X_2$ are —O—, and the physiologically tolerated salts thereof.

4. A compound of formula (I) as claimed in claim 1, which is a compound of formula (IV)

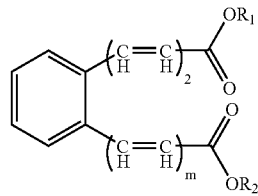

wherein m is 3 or 4, and $R_1$ and $R_2$ are as defined in claim 1 and the physiologically tolerated salts thereof.

5. A compound of formula (V)

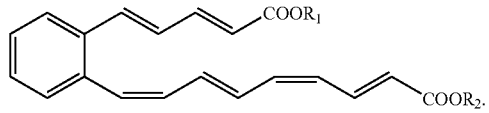

wherein $R_1$ and $R_2$ are independently of each other, H, $C_1$-$C_6$-alkyl, $C_2$-$C_6$-alkenyl, $C_2$-$C_6$-alkynyl or $C_5$-$C_{14}$-aryl, in which alkyl, alkenyl, alkynyl and aryl are unsubstituted or substituted, once or twice, by a substituent independently selected from —OH, —O—$C_1$-$C_6$-alkyl, —O—$C_2$-$C_6$-alkenyl, —O—$C_5$-$C_{14}$-aryl, $C_5$-$C_{14}$-aryl, —NH—$C_1$-$C_6$-alkyl, —NH—$C_2$-$C_6$alkenyl, —$NH_2$ and halogen, in which alkyl, alkenyl, alkynyl and aryl are independently unsubstituted or substituted, once or twice, by a substituent independently selected from —OH, =O, —O—$C_1$-$C_6$-alkyl, —O—$C_2$-$C_6$-alkenyl, —O—$C_5$-$C_{14}$-aryl, $C_5$-$C_{14}$-aryl, —NH—$C_1$-$C_6$-alkyl, —NH—$C_2$-$C_6$-alkenyl, —$NH_2$ and halogen, in which said alkyl, alkenyl, alkynyl and aryl can be further independently substituted by a —CN, amide or oxime.

6. A compound of formula (V) as claimed in claim 5, wherein each of $R_1$ and $R_2$ is H.

7. A compound of formula (I) as claimed in claim 1, which is a compound of formula (VI)

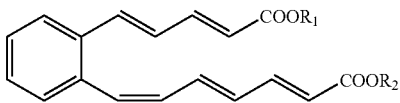
(VI)

wherein R1 and R2 are as defined in claim 1.

8. A compound of formula (VI)

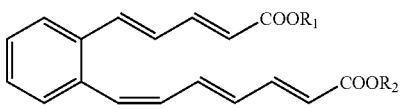
(VI)

wherein $R_1$ and $R_2$ are each H.

9. A compound of formula (I) as claimed in claim 1, which is a compound of formula (VII)

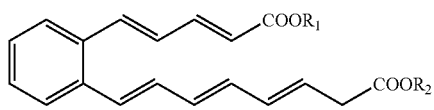
(VII)

wherein R1 and R2 are as defined in claim 1.

10. A compound of formula (VII)

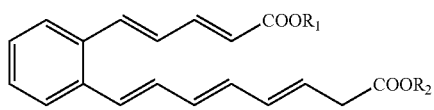
(VII)

wherein $R_1$ and $R_2$ are each H.

11. A compound of formula (I) as claimed in claim 1, which is a compound of formula (VIII)

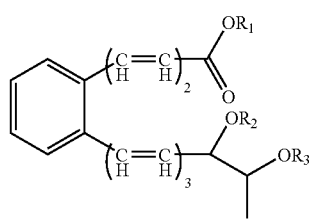
(VIII)

wherein R1 and R2 are as defined in claim 1.

12. A compound of formula (VIII) as claimed in claim 11, which is a compound of formula (IX)

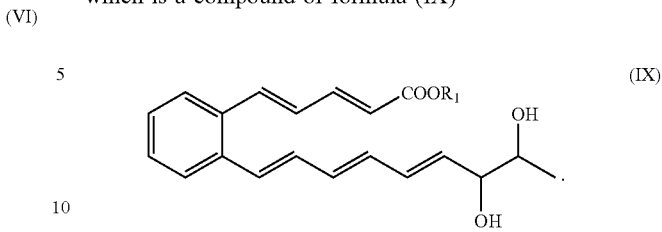
(IX)

13. A compound of formula (IX) as claimed in claim 12, wherein $R_1$ is H.

14. A compound of the formula (VIII) as claimed in claim 11, which is a compound of formula (X)

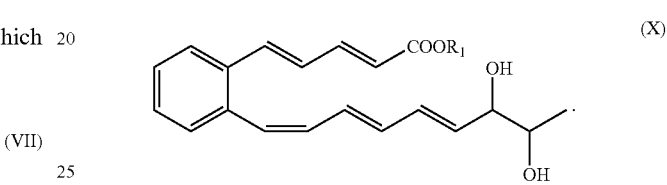
(X)

15. A compound of formula (X) as claimed in claim 14, wherein $R_1$ is H.

16. A process for preparing a compound of formula (I) as claimed in claim 1, which comprises 1. culturing the microorganism *Actinomycetales* sp. DSM 14865, in an aqueous nutrient medium until one or more of the compounds serpentemycin A, B, C and D accrues in the culture broth, and 2. isolating and purifying said serpentemycin A, B, C and/or D.

17. A process as claimed in claim 16, which comprises fermenting the microorganism *Actinomycetales* sp. DSM 14865 in a culture medium which contains a carbon and nitrogen source and also the customary inorganic salts and trace elements, isolating serpentemycins A, B, C and/or D and, where appropriate, converting said serpentemycins A, B, C and/or D into a pharmacologically tolerated salt.

18. A process as claimed in claim 16, wherein the fermentation is carried out under aerobic conditions at a temperature of between 20 and 35° C. and at a pH between 4 and 10.

19. The Isolated microorganisms *Actinomycetales* sp., DSM 14865.

\* \* \* \* \*